United States Patent
Okamoto et al.

(10) Patent No.: US 7,740,758 B2
(45) Date of Patent: Jun. 22, 2010

(54) SEPARATING AGENT INCLUDING POLYSACCHARIDE DERIVATIVE HAVING A POLYCYCLIC STRUCTURE

(75) Inventors: Yoshio Okamoto, Aichi (JP); Chiyo Yamamoto, Aichi (JP)

(73) Assignee: Daicel Chemical Industries, Ltd., Sakai-shi, Osaka (JP)

( * ) Notice: Subject to any disclaimer, the term of this patent is extended or adjusted under 35 U.S.C. 154(b) by 932 days.

(21) Appl. No.: 11/542,458

(22) Filed: Oct. 3, 2006

(65) Prior Publication Data

US 2007/0029242 A1    Feb. 8, 2007

Related U.S. Application Data

(62) Division of application No. 10/467,201, filed as application No. PCT/JP02/04160 on Apr. 25, 2002, now Pat. No. 7,156,989.

(30) Foreign Application Priority Data

Apr. 27, 2001    (JP)    ............... 2001-131942

(51) Int. Cl.
 *B01D 15/08*    (2006.01)
(52) U.S. Cl. ............ 210/198.2; 210/502.1; 210/635; 210/656; 502/404; 536/18.7; 536/123.1
(58) Field of Classification Search ........ 210/635, 210/656, 198.2, 502.1; 502/404; 536/18.7, 536/123.1
See application file for complete search history.

(56) References Cited

U.S. PATENT DOCUMENTS

| | | | | | |
|---|---|---|---|---|---|
| 4,818,394 | A | * | 4/1989 | Okamoto et al. | ......... 210/198.2 |
| 5,091,520 | A | * | 2/1992 | Francotte et al. | .............. 536/56 |
| 5,496,937 | A | * | 3/1996 | Okamoto et al. | ............ 536/124 |
| 5,679,572 | A | * | 10/1997 | Okamoto et al. | ............ 210/656 |
| 5,770,088 | A | * | 6/1998 | Ikeda et al. | ................. 210/659 |
| 6,277,782 | B1 | * | 8/2001 | Moller et al. | ............... 502/402 |
| 6,372,142 | B1 | * | 4/2002 | Gjerde et al. | ............... 210/635 |
| 6,533,936 | B1 | * | 3/2003 | Ikeda | ......................... 210/635 |

FOREIGN PATENT DOCUMENTS

| | | |
|---|---|---|
| EP | 0 156 382 A2 | 10/1985 |
| EP | 0 527 236 A1 | 2/1993 |
| WO | WO 97/49733 | 12/1997 |

* cited by examiner

*Primary Examiner*—Ernest G Therkorn
(74) *Attorney, Agent, or Firm*—Flynn, Thiel, Boutell & Tanis, P.C.

(57) ABSTRACT

The present invention provides a separating agent for enantiomeric isomers, which has an excellent ability to identify asymmetry. That is, the present invention relates to a separating agent for enantiomeric isomers which includes as an effective component a polysaccharide derivative having a bicyclic or more structure having an aromatic, alicyclic, or heterocyclic ring.

4 Claims, No Drawings

SEPARATING AGENT INCLUDING POLYSACCHARIDE DERIVATIVE HAVING A POLYCYCLIC STRUCTURE

REFERENCE TO RELATED APPLICATIONS

This is a division of Ser. No. 10/467,201, filed Aug. 5, 2003 now U.S. Pat. No. 7,156,989, which was the national stage of International Application No. PCT/JP02/04160, filed Apr. 25, 2002, which International Application was not published in English.

TECHNICAL FIELD TO WHICH THE INVENTION BELONGS

The present invention relates to a separating agent including as an effective component a polysaccharide derivative having a bicyclic or more structure containing an aromatic ring, an alicyclic ring, or a heterocyclic ring (hereinafter referred to as a polycyclic structure) and to an enantiomeric isomer separating agent that is used for separation of various chemical substances, in particular, for optical resolution.

PRIOR ART

Many organic compounds have enantiomeric isomers that have the same physical and chemical properties as one another, for example, boiling point, melting point and solubility, but are different from one another in physiological properties. This is because proteins and glucides by themselves that constitute an organism in most cases are composed of one enantiomeric isomer and there arises a difference in the manner of action on the other enantiomeric isomer and thus a difference in physiological activity arises. In particular, in the field of medicine, it is often the case that enantiomeric isomers have a significant difference in efficacy or toxicity. For this reason, the Ministry of Health, Labour and Welfare of Japan prescribes in the Guideline for the Production of Medicines that "in the case where the drug is a racemic form, it is desirable that the dynamic behaviors of absorption, distribution, metabolism and excretion be made on each isomer".

As described above, since physical properties and chemical properties, for example, the boiling point, melting point and solubility, of the enantiomeric isomers are quite the same, they cannot be analyzed by the ordinary separation means. Accordingly, studies on the technology of analyzing a wide variety of enantiomeric isomers simply and with high precision have been intensively made. As an analytical technique in response to these requirements, an optical separation method by high performance liquid chromatography (HPLC), in particular an optical separation method by a chiral column for HPLC has been advanced. The chiral column as used herein is an asymmetry identifying agent by itself or a chiral immobilizing phase including an asymmetry identifying agent used as carried on a suitable carrier.

For example, optically active poly(triphenylmethyl methacrylate) (JP 57-150432 A), cellulose, amylose derivative (Y. Okamoto, M. Kawashima and K. Hatada, J. Am. Chem. Soc., 106, 5337, 1984), and ovomucoid (JP 63-307829 A), which is a protein, have been developed. Among the many chiral immobilizing phases for HPLC, optical resolution columns that carry cellulose or an amylose derivative on silica gel are known to have high asymmetry identifying ability for a very wide variety of compounds. In recent years, studies have been advanced on preparative liquid chromatography for an optically active substance on an industrial scale by using a chiral immobilizing phase for HPLC and a simulated moving bed chromatography in combination (Phram Tech Japan, 12, 43), and not only to fully separate but also to increase the productivity of preparative chromatography, a chiral immobilizing phase has been demanded that performs further improved separation of the target compound of preparative separation, that is, has a greater value of separation coefficient α.

Also, recently, associated with the orientation in the art toward micro analysis technologies, enantiomeric isomer separation thin layer chromatography (chiral TLC) that is capable of performing the separation of enantiomeric isomers by a separation operation simpler than enantiomeric isomer separation in the field of capillary electrophoresis (CE) or HPLC has received high attention. Accordingly, application of polysaccharide derivatives having high asymmetry identifying ability to these fields of the art has been demanded.

DISCLOSURE OF THE INVENTION

The inventors of the present invention have made extensive research with a view to solving the above-mentioned problems, and as a result they have found that a polysaccharide derivative having a sterically bulky polycyclic structure has excellent asymmetry identifying ability, thereby achieving the present invention.

Therefore, the present invention relates to a separating agent for enantiomeric isomers including as an effective component a polysaccharide derivative having a polycyclic structure.

The present invention provides use of a polysaccharide derivative containing a bicyclic or more structure (hereinafter referred to as a polycyclic structure) containing an aromatic ring, an alicyclic ring or a heterocyclic ring as a separating agent for enantiomeric isomers and a method of separating enantiomeric isomers with a polysaccharide derivative containing a bicyclic or more structure (hereinafter referred to a polycyclic structure) containing an aromatic ring, an alicyclic ring or a heterocyclic ring.

DETAILED DESCRIPTION OF THE INVENTION

Hereinafter, description will be made of embodiments of the present invention in detail.

As a polysaccharide that constitutes a polysaccharide derivative having a polycyclic structure used in the present invention, any synthetic polysaccharide, any natural polysaccharide, and any modified natural polysaccharide may be used so long as they have an optical activity. Those which have a high regularity for the binding form are more desired. There are exemplified β-1,4-glucan (cellulose), α-1,4-glucan (amylose, amylopectin), α-1,6-glucan (dextran), β-1,6-glucan (busturan), β-1,3-glucan (for example, cardran, schizophyllan, etc.), α-1,3-glucan, β-1,2-glucan (Crown Gall polysaccharide), β-1,4-galactan, β-1,4-mannan, α-1,6-mannan, β-1,2-fructan (inulin), β-2,6-fructan (levan), β-1,4-xylan, β-1,3-xylan, β-1,4-chitosan, α-1,4-N-acetylchitosan (chitin), pullulan, agarose, alginic acid, and the like. Also, the polysaccharide includes starch containing amylose. Among those, cellulose, amylose, β-1,4-xylan, β-1,4-chitosan, chitin, β-1,4-mannan, inulin, and cardran, which are readily available as the polysaccharide having high purity, are preferred. Cellulose and amylose are particularly preferred.

These polysaccharides have a number average degree of polymerization (an average number of pyranose rings or furanose rings contained in one molecule) of 5 or more, preferably 10 or more and desirably 1,000 or less in consideration of ease of handling although there is no particular upper limit.

In the present invention, polysaccharide derivatives refer to compounds including a polysaccharide with a part or all of the hydroxyl groups thereof bonded to a compound having a functional group reactive with the hydroxyl group or groups through an ester bond, an urethane bond or an ether bond, with a carbamate derivative or an ester derivative thereof being preferable. Particularly preferred polysaccharide derivatives used in the present invention are ester derivatives or carbamate derivatives of polysaccharides having 0.1 or more ester bond or urethane bond per 1 glucose unit and the carbamate derivatives are more preferably used.

In the present invention, the polycyclic structure means a bicyclic or more structure containing an aromatic ring, an alicyclic ring or a heterocyclic ring, with a structure containing an aromatic ring being preferable. The number of rings bonded is not particularly limited but a bicyclic ring is preferable. Specific examples of the group having a polycyclic structure include a fluorenyl group, an indanyl group, an anthryl group, a pyrenyl group, a phenanthryl group, a quinolyl group, a pentarenyl group, an indenyl group, a naphthyl group, an azurenyl group, and a heptanyl group.

The polysaccharide derivative having a polycyclic structure used in the present invention can be obtained by reacting a polysaccharide with a compound having a polycyclic structure and a functional group reactive with a hydroxyl group of the polysaccharide to form an ester bond, an urethane bond, an ether bond or the like. The compound having a polycyclic structure and a functional group reactive with a hydroxyl group of the polysaccharide includes those compounds that have a functional group reactive with the above-mentioned hydroxyl group and further have the above-mentioned polycyclic structure, for example, 9H-furorenyl isocyanate and 5-indanyl isocyanate.

The polysaccharide derivative having a polycyclic structure of the present invention is a substance that is an extremely useful substance as a functional material and is useful as an enantiomeric isomer separating agent, in particular, a chiral immobilizing phase for chromatography. To use the polysaccharide derivative of the present invention as a separating agent in the separation of compounds or enantiomeric isomers, generally it is used in chromatographic methods such as a gas chromatographic method, a liquid chromatographic method, a thin layer chromatographic method, a supercritical chromatographic method, a capillary electrophoretic method, and a continuous liquid preparative chromatographic method. In addition, it is also possible to perform membrane separation by carrying it on a membrane.

As the chiral immobilizing phase for chromatography using the polysaccharide derivative of the present invention, an immobilizing phase for liquid chromatography, an immobilizing phase for thin layer chromatography, an asymmetry identifying agent added to an electrophoretic solution in capillary electrophoresis represented by a micelle electroconductive chromatographic method, and immobilizing phase for preparative continuous liquid chromatography represented by a simulated moving bed chromatography are preferable.

To apply the separating agent of the present invention to a liquid chromatography method, there is a method for filling the separating agent as a powder in a column, a method of coating it on a capillary column, a method of forming a capillary with the separating agent and utilizing the inner wall thereof, and so on. Generally, the separating agent is converted to a powder. To convert the separating agent into a powder, it is preferred that the separating agent be pulverized or made into the form of beads. The size of the particles may vary depending on the size of the column to be used, and the particle size is preferably 1 µm to 10 mm, and more preferably 1 µm to 300 µm. The particles are preferably porous.

Further, in order to improve the pressure resistance property of the separating agent, prevent swelling or contraction of the separating agent by substitution of solvents, and increase the theoretical number of stages, it is preferred that the separating agent be held on a carrier. The size of the carrier may vary depending on the size of the column or plate to be used; generally the size is 1 µm to 10 mm, and more preferably 1 µm to 300 µm. The carrier is preferably porous and has an average pore diameter of preferably 10 Å to 100 µm, and more preferably 50 Å to 50,000 Å. The carrying amount of the separating agent is 1 to 100% by weight, preferably 5 to 50% by weight based on the carrier.

The method of carrying the polysaccharide derivative to the carrier may be either a chemical method or a physical method. As the chemical method, there is a method in which part of hydroxyl groups are protected at the time of forming derivative of the polysaccharide and after the derivative is formed, deprotection is performed and the deprotected hydroxyl group and silica gel are chemically bonded (Y. Okamoto et al., J. Liq. Chromatogr., 10 (8&9), 1613, 1987). As the physical method, there is a method in which the polysaccharide derivative is dissolved in a solvent in which the polysaccharide derivative is soluble and rendered well mixed with the carrier and the solvent is distilled off under a reduced pressure, under warming or under an air stream or the like.

As the carrier, mention may be made of a porous organic carrier and a porous inorganic carrier. The porous inorganic carrier is preferable. Suitable examples of the porous organic carrier include polymer substances such as polystyrene, polyacrylamide, and polyacrylate. Suitable examples of the porous inorganic carrier include synthetic or natural substances such as silica, alumina, magnesia, titanium oxide, glass, silicates, and kaolin. To improve its affinity for the polysaccharide derivative, the carrier may be subjected to a surface treatment. The method of the surface treatment includes a silane treatment with an organosilane compound or a surface treatment with plasma polymerization, and so on.

EFFECT OF THE INVENTION

According to the present invention, an enantiomeric isomer separating agent having a high asymmetry identifying ability can be provided.

EXAMPLES

The present invention will be described in detail by examples. However, the present invention should not be considered as being limited to these examples.

Example 1

[1] Synthesis of cellulose tris(9H-fluorenyl carbamate) (1a)

After 0.30 g of cellulose (trade name: Avicell, manufactured by Merck Co.) and 0.21 g of lithium chloride were dried for 3 hours, 2.0 ml of dimethylacetamide (DMA) was added thereto and allowed to swell at 90° C. to 100° C. for one night. Thereafter, 6.0 ml of pyridine was added and 1.3 equivalents of 9H-fluorenyl isocyanate was added and allowed to react for 6 hours. A carbamate derivative was deposited by reprecipitation from the reaction mixture and filtered through a glass filter, and then dried under vacuum to obtain 1.16 g of cellulose tris(9H-fluorenyl carbamate) represented by the formula (1a). The elemental analysis values of the obtained (1a) are shown in Table 1.

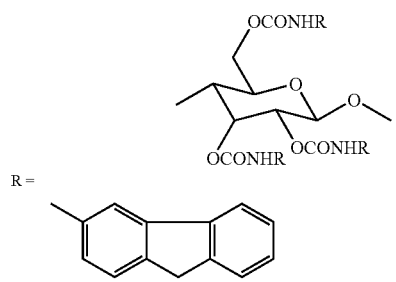

(1a)

[2] Fabrication of a Filler by Carrying (1a) on Silica Gel 0.75 g of the carbamate derivative (1a) obtained in [1] was dissolved in 10 ml of tetrahydrofuran (THF) and the solution was perfused uniformly on 3 g of silica gel (manufactured by Daiso Co., Ltd., particle size of 7 μm, thin-pore diameter of 1,000 Å), and then the solvent was distilled off to fabricate a filler on which cellulose tris(9H-fluorenyl carbamate) (1a) was carried.

[3] Fabrication of a Column Filled with a Filler by Carrying (1a) on Silica Gel 2.5 g of the carried type filler fabricated in [2] was pressed and filled into a stainless steel-made column of ϕ 0.46 cm×L 25 cm by a slurry filling method to fabricate a separation column for enantiomeric isomers.

Example 2

[1] Synthesis of cellulose tris(5-indanyl carbamate) (1b)

After 0.20 g of cellulose (trade name: Avicell, manufactured by Merck Co.) and 0.15 g of lithium chloride were dried for 3 hours, 1.5 ml of DMA was added thereto and allowed to swell at 90° C. to 100° C. for one night. Thereafter, 5.0 ml of pyridine was added and 1.5 equivalents of 5-indanyl isocyanate was added and allowed to react for 6 hours. A carbamate derivative was deposited by reprecipitation from the reaction mixture and filtered through a glass filter, and then dried under vacuum to obtain 0.53 g of cellulose tris(5-indanyl carbamate) represented by the formula (1b). The elemental analysis values of the obtained (1b) are shown in Table 1.

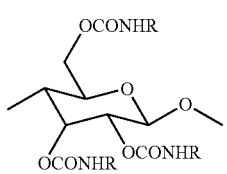

(1b)

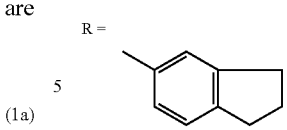

[2] Fabrication of a Filler by Carrying (1b) on Silica Gel

The carbamate derivative (1b) obtained in [1] was used to fabricate a filler on which cellulose tris(5-indanyl carbamate) (1b) was carried in the same manner as in [2] of Example 1.

[3] Fabrication of a Column Filled with a Filler by Carrying (1b) on Silica Gel

The carried type filler fabricated in [2] was filled into a stainless steel-made column of ϕ 0.20 cm×L 25 cm in the same manner as in [3] of Example 1 to fabricate a separation column for enantiomeric isomers.

Example 3

[1] Synthesis of amylose tris(5-indanyl carbamate) (2b)

After 0.20 g of amylose (trade name: AS-50, manufactured by Ajinoki Co., Ltd.) and 0.15 g of lithium chloride were dried for 3 hours, 1.5 ml of DMA was added thereto and allowed to swell at 90° C. to 100° C. for one night. Thereafter, 6.0 ml of pyridine was added and 1.6 equivalents of 5-indanyl isocyanate was added and allowed to react for 6 hours. A carbamate derivative was deposited by reprecipitation from the reaction mixture and filtered through a glass filter, and then dried under vacuum to obtain 0.69 g of amylose tris(5-indanyl carbamate) represented by the formula (2b). The elemental analysis values of the obtained (2b) are shown in Table 1.

(2b)

[2] Fabrication of a Filler by Carrying (2b) on Silica Gel

The carbamate derivative (2b) obtained in [1] was used to fabricate a filler on which amylose tris(5-indanyl carbamate) (2b) was carried in the same manner as in [2] of Example 1.

[3] Fabrication of a Column Filled with a Filler by Carrying (2b) on Silica Gel

The carried type filler fabricated in [2] was used and filled into a stainless steel-made column of ϕ 0.20 cm×L 25 cm in the same manner as in [3] of Example 1 to fabricate a separation column for enantiomeric isomers.

TABLE 1

|  |  | Elemental analysis result | | |
|---|---|---|---|---|
|  |  | C % | H % | N % |
| (1a) | Calculated value | 73.55 | 4.76 | 5.36 |
|  | Analysis value | 71.95 | 4.98 | 5.13 |
| (1b) | Calculated value | 67.59 | 5.83 | 6.57 |
|  | Analysis value | 65.49 | 5.75 | 6.26 |
| (2b) | Calculated value | 67.59 | 5.83 | 6.57 |
|  | Analysis value | 66.19 | 5.76 | 6.44 |

Comparative Example 1

By using cellulose trisphenyl carbamate as a separating agent, an enantiomeric isomer separation column was fabricated by the same method as that in Example 1 in JP 60-108751 A.

Application Example 1

By using the columns fabricated in Examples 1 to 3 and Comparative Example 1, optical resolution of racemic forms (a) to (g) described below was performed by a liquid chromatographic method under the conditions described below. The results are shown in Table 2.

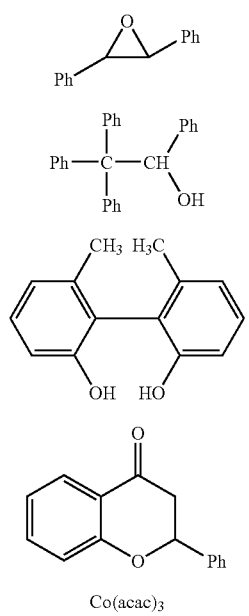

Racemic form (a)

Racemic form (b)

Racemic form (c)

Racemic form (d)

Racemic form (e)

Racemic form (f)

Racemic form (g)

<Analysis Conditions>
Moving phase: Hexane/isopropanol=90/10 (v/v)
Flow rate: 0.5 ml/min for the columns of Example 1 and Comparative Example 1 and 0.1 ml/min for the columns of Examples 2 and 3

Temperature: 25° C.
Detection: 254 nm
Note that the separation coefficient (α) in the table is defined as follows.

$\alpha = k_2'/k_1'$

Here, $k_1'$ is the holding coefficient of a relatively weakly held enantiomeric isomer, and $k_2'$ is the holding coefficient of a relatively strongly held enantiomeric isomer.

TABLE 2

| Target racemic form for separation | Separation coefficient (α) | | | |
|---|---|---|---|---|
|  | Example 1 | Example 2 | Example 3 | Comparative Example 1 |
| (a) | 1.56 | 1.41 | 1.46 | 1.19 |
| (b) | to 1 | 1.25 | 1.49 | 1.0 |
| (c) | 1.26 | 1.78 | 1.30 | 1.47 |
| (d) | to 1 | 1.21 | 1.41 | to 1 |
| (e) | to 1 | 1.5 | to 1 | 1.0 |
| (f) | 1.14 | 1.67 | to 1 | 1.52 |
| (g) | to 1 | 1.57 | 1.21 | to 1 |

What is claimed is:
1. A separating agent for enantiomeric isomers comprising cellulose tris (5-indanylcarbamate supported on a carrier suitable for chromatographic separation.
2. The separating agent according to claim 1, wherein the separating agent is adapted to be used as a chiral immobilizing phase for chromatography.
3. The separating agent according to claim 2, wherein the chiral immobilizing phase for chromatography is adapted to be used for an immobilizing phase for liquid chromatography.
4. The separating agent according to claim 2, wherein the chiral immobilizing phase for chromatography is adapted to be used for an immobilizing phase for a preparative continuous liquid chromatography.

* * * * *